United States Patent [19]
Volkov et al.

[11] 3,985,127
[45] Oct. 12, 1976

[54] APPARATUS FOR SURGICAL TREATMENT OF THE KNEE JOINT

[76] Inventors: Mstislav Vasilievich Volkov, 1 Stroitelnaya ulitsa, 6, korpus 1, kv. 63; Oganes Vardanovich Oganesian, ulitsa Pervomaiskaya, 74, kv. 87, both of Moscow, U.S.S.R.

[22] Filed: June 11, 1975

[21] Appl. No.: 586,134

[52] U.S. Cl. .............................. 128/84 R; 128/92 A
[51] Int. Cl.² ............................................ A61F 5/04
[58] Field of Search .............. 128/84 R, 84 A, 84 B, 128/84 C, 92 R, 92 A

[56] References Cited
UNITED STATES PATENTS

| | | | |
|---|---|---|---|
| 2,238,869 | 4/1941 | Haynes | 128/92 A |
| 2,346,346 | 4/1944 | Anderson | 128/92 A |
| 2,391,537 | 12/1945 | Anderson | 128/84 B |
| 2,687,720 | 8/1954 | Haboush | 128/84 R |

FOREIGN PATENTS OR APPLICATIONS

| | | | |
|---|---|---|---|
| 240,918 | 8/1969 | U.S.S.R. | 128/92 R |

*Primary Examiner*—John D. Yasko
*Attorney, Agent, or Firm*—Steinberg and Blake

[57] ABSTRACT

The proposed apparatus for surgical treatment of the knee joint comprises two pairs of needles each of which is to be driven through one of the joint ends. Each pair of needles is secured in at least one brace so that each pair of needles forms a rigid system with the brace, said rigid system being secured on the respective joint end. The two rigid systems are interconnected by means of distractors which are rigidly coupled to one of said systems and connected to the other one by way of a four-bar mechanism.

The proposed apparatus permits exactly reproducing the movement of the knee joint, and between the joint ends there is provided a permanent minimal gap of preset magnitude completely obviating all friction between the joint surfaces.

4 Claims, 3 Drawing Figures

APPARATUS FOR SURGICAL TREATMENT OF THE KNEE JOINT

The present invention relates to medical technology, and, more particularly, to apparatus for surgical treatment of the knee joint.

The proposed apparatus may find application in orthopaedics and traumatology for correcting irreducible and inveterate dislocations of the leg bones and subsequently restituting movement in the knee joint, for eliminating knee-joint contractures, and for fixing periarticular and diaphyseal fractures as well as false joints of the tibia and femur with simultaneous restitution of movement in the knee joint.

Widely known in the art are apparatus for surgical treatment of joints which comprise at least two pairs of needles. The tips of the needles of each pair are secured in one brace or in two rigidly interconnected braces so that each pair of needles forms a rigid system with the brace(s). The needles of each rigid system are driven through one of the bones being aligned. Said rigid systems are interconnected by means of distractors which permit varying the distance between these systems. The distractors are fixed to one rigid system of needles and braces and connected to the other rigid system by means of an articulated device simulating joint movement. Thus it is known in the art to employ an apparatus for surgical treatment of the knee joint which comprises two braces, with self-aligning cylinders having adapters for tensioning a pair of needles with threaded tips being disposed at the feet of said braces. One brace of the apparatus, known as an axial brace, serves to fix the distal end of the femur with the aid of an axial needle driven through the pivot of the joint and a locking needle driven through the joint end through which passes the pivotal axis of the joint. The other brace of the apparatus, known as a rotary brace, serves to fix the other joint end, in this case the proximal end of the tibia, which is likewise achieved by use of a pair of needles. The two braces are interconnected by distractors which are fixed to the rotary brace and coupled to the axial brace by means of a polycentric mechanism simulating the movement of the knee joint. Said mechanism is formed as a gear wheel fixed on the axial needle of the axial brace, which is mounted on the distal end of the femur, and cooperating with a gear segment rigidly coupled with the rotary brace. The gear wheel is connected with the gear segment by means of two connecting rods.

The braces of the apparatus are interconnected at the top by means of a bending-unbending device permitting gradual and measured relative rotation of the braces and, hence, of the joint ends.

Application of said prior art apparatus starts by driving the axial needle along the main plane of motion of the joint through those points of the femoral joint end which describe the least curve in the course of flexion and extension. After the the axial needle has been driven home, the locking needle is driven through the points corresponding to the points of its attachment in the apparatus. Then two needles are driven through the proximal end of the tibia, after which all the needles are tensioned and fixed in the apparatus.

After the apparatus has been applied, the distance between the braces is varied with the aid of split nuts serving to fasten the distractors to the rotary brace, thereby setting up a gap of predetermined magnitude between the joint ends, and the bending-unbending device is manipulated to gradually and proportionately turn one brace with its needles relative to the other brace, thereby training and restituting movement in the joint.

The chief disadvantage of the prior art apparatus in question consists in that the gear wheel cooperating with the gear segment fails to reproduce sufficiently precisely the flexion and extension of the knee joint; nor does it provide for the permanence of the gap between the joint ends in motion. A further disadvantage of this apparatus is inadequate smoothness of movement in the gear coupling of the distractors.

It is an object of the present invention to provide an for surgical apparatus treatment of the knee joint which would be capable of precisely reproducing the flexion and extension of the knee joint.

It is another object of the present invention to provide an apparatus which would permit totally removing the dynamic load off the joint, maintaining a permanent minimal gap of predetermined size between the joint ends.

It is a further object of the present invention to provide an apparatus wherein the braces thereof turn smoothly, ensuring active and passive movements in the joint unloaded by the apparatus.

The foregoing objectives are attained in an apparatus for surgical treatment of the knee joint, comprising two pairs of needles each of which is designed to be driven through one of the joint ends, each pair of needles being secured in at least one brace so that each pair of needles and the brace form a rigid system to be secured on the respective joint end, and also comprising distractors interconnecting said rigid systems, which distractors are fixed to one rigid system and connected to the other one by way of a polycentric mechanism, wherein, in accordance with the invention, the polyconcentric mechanism is formed as a four-bar mechanism.

The apparatus of this invention has a wider functional scope than the prior art apparatus. Thus, it is capable of precisely reproducing the movement of the knee joint, simultaneously maintaining a permanent minimal gap of predetermined magnitude between the joint ends, which permits completely obviating all friction between the joint surfaces.

The proposed apparatus enables joint contracture to be gradually and proportionately corrected to the point where the joint function is restituted in the entire flexion-extension range. In the course of contracture correction, the correcting effort is distributed between the joint ends in accordance with the biomechanics of each individual joint. All these features combine to make for a more physiological restitution of the function of the damaged knee joint within a shorter period of time, and to prevent invalidism.

The invention will be further understood from the following description of an exemplary embodiment thereof taken in conjunction with the accompanying drawings, wherein.

Figure 1:
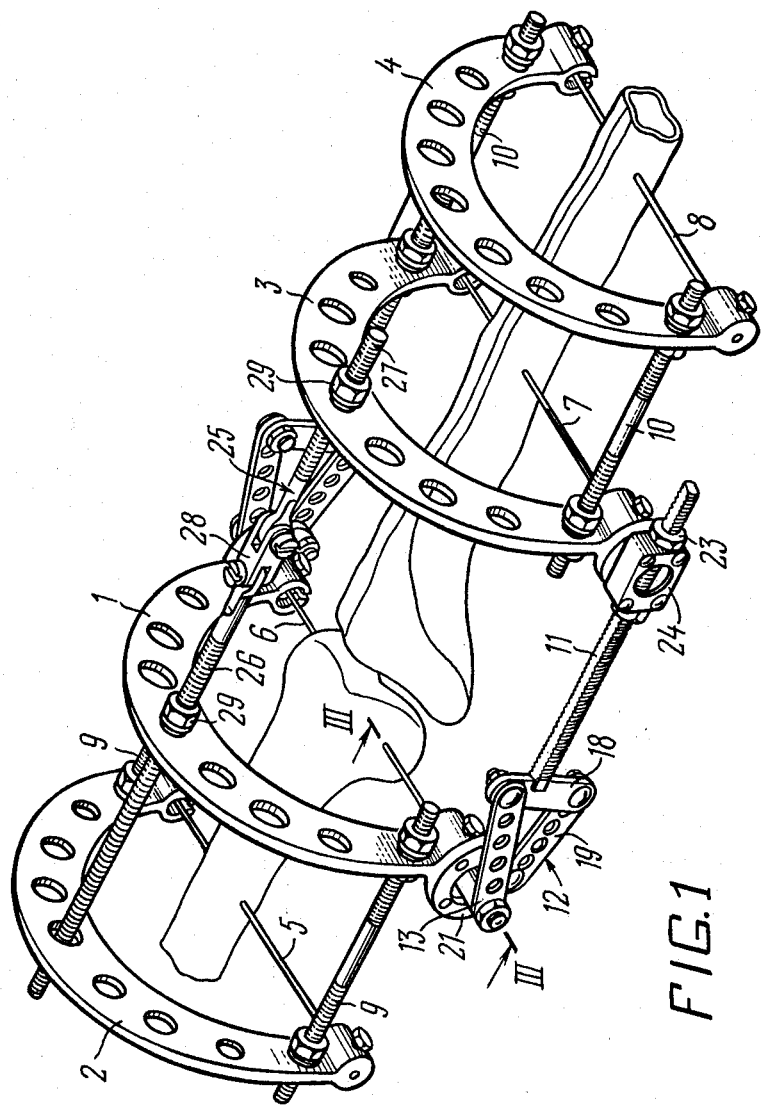
FIG. 1 is a general view of an apparatus for surgical treatment of the knee joint, in accordance with the invention.

Referring now to the drawings, the proposed apparatus comprises four interconnected braces: a supporting brace 1, a locking brace 2 and two rotary braces 3 and 4. Needles 5, 6, 7 and 8 are tensioned and fixed, one in each, in the braces 1, 2, 3 and 4, respectively, the needles 5, 6, 7 and 8 being designed to be driven through the bones aligned. The supporting brace 1 and the locking brace 2 are rigidly interconnected by two tie bolts 9, whereas the rotary braces 3 and 4 are rigidly interconnected by two tie bolts 10. A pair of needles may likewise be secured in a single brace (not shown).

The pair of needles 5 and 6 with the braces 1 and 2 define one rigid system designed to be secured on one joint end, while the pair of needles 7 and 8 together with the braces 3 and 4 define a second rigid system to be secured on the other joint end.

The two rigid systems are interconnected by two distractors 11 each of which is secured at one end to the brace 3 and connected to the brace 1 by way of a polycentric mechanism reproducing the movement of the knee joint. The polycentric mechanism is formed as a four-bar linkage mechanism or means 12.

Figure 2:
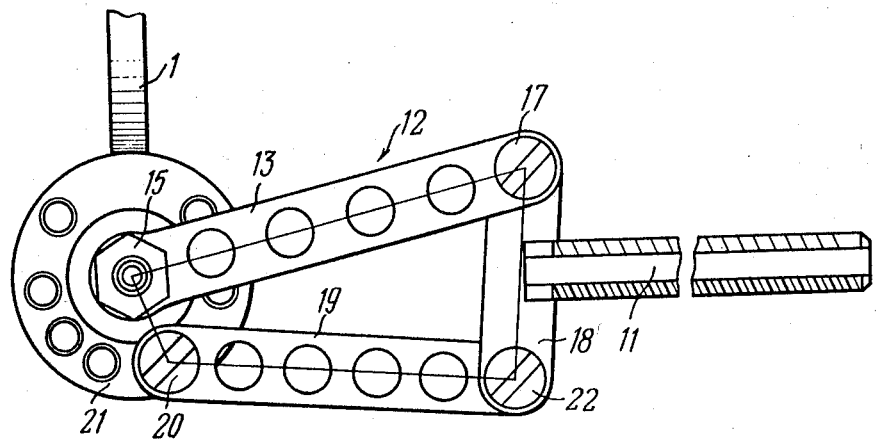
FIG. 2 is a side elevation of a four-bax mechanism, in accordance with the invention (blown-up view)
Figure 3:
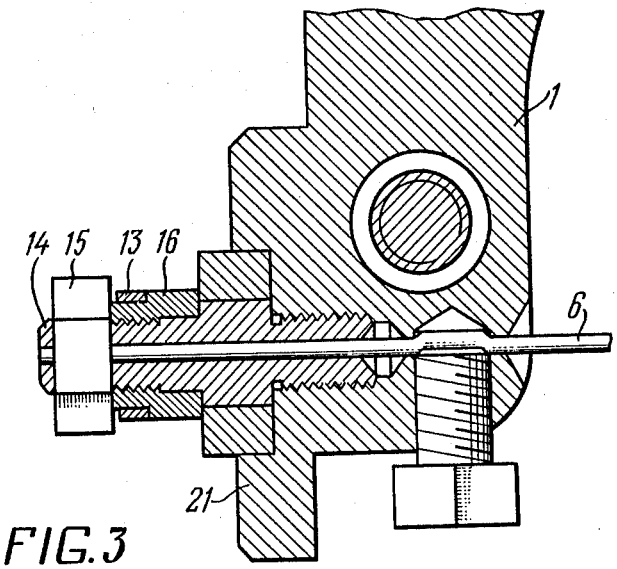
FIG. 3 is a sectional view taken on the line III—III in FIG. 1.

Bar or link 13 (FIG. 2) of the four-bar mechanism 12 is pivotally connected at one end with a screw 14 (FIG. 3) of the axial needle 6 by means of a nut 15 and a bush 16 fitted over the screw 14, and at the other end with bar 18 of the four-bar mechanism 12 by means of a pivot 17 (FIG. 2), the bar 18 being fixed to and in effect forming a portion of the distractor 11. Bar or link 19 of the four-bar mechanism 12 is connected at one end with bar 21 by means of a pivot 20, the bar 21 being a portion of brace 1; at the other end, the bar 19 is pivotally connected with the bar 18 at 22. The other end of the distractor 11 is attached to the brace 3 with the aid of split nuts 23 (FIG. 1) and a box 24 fixed by screws to the brace 3, thereby enabling the distance between the rigid systems, and hence between the joint ends secured therein, to be varied. The braces 1 and 3 are interconnected at the top by means of a bending-unbending device 25 formed as two rods 26 and 27 interconnected by a universal joint 28. The bending-unbending device 25 is locked in position with the aid of nuts 29. The bending-unbending device 25 serves to train and restitute the flexion-extension function of the joint.

The apparatus for surgical treatment of the knee joint functions as follows.

Application of the apparatus starts by driving the axial needle 6 through the femur 2.5 cm above the gap between the joint ends. The axial needle 6 is fixed in the supporting brace 1. Then, with the axial needle 6 is position, the needle 5 is driven through the diaphysis of the bone in the frontal plane and secured in the brace 2. Then the other two needles, 7 and 8, are driven through the tibia and secured in the braces 3 and 4. If the trauma is contracture, movement training can be initiated immediately upon application of the apparatus.

After the joint ends have been spaced apart a predetermined distance with the aid of the split nuts 23, the bending-unbending device 25 is used to eliminate the contracture and to train and restitute the movement of the joint.

The apparatus having been applied, the joint secured in the apparatus is flexed and extended for 20 to 30 days, 2 to 6 degrees a day depending on the type and duration of the contracture and the type of joint. After 10 to 15 flexion-extension cycles, the time of flexion and extension is gradually reduced until it reaches only a few minutes, at which point the bending-unbending device 25 is removed, following which the patient performs active movements in the apparatus for several days, and then the apparatus is removed.

In contracture correction, the apparatus performs a dual function: the distractors 11 of the apparatus are used for spacing the joint surfaces a predetermined distance apart, thereby obviating any possibility of their compression; the bending-unbending device 25 is used to perform a gradual and measured flexion-extension motion of the joint ends secured in the apparatus. It is very important that the effort mounted by the apparatus for contracture correction is distributed between the joint ends in precise accordance with the biomechanics of the knee joint. All these features are paramount for a more physiological contracture correction followed by the restitution of joint movement.

The four-bar mechanism 12 employed in the apparatus of this invention provides for smooth movement in the pivots and enables the flexion-extension function of the knee joint to be exactly reproduced; furthermore, it completely relieves the joint of dynamic loading, helps maintain a permanent minimal gap between the joint ends and facilitates active and passive movements of the joint unloaded by the apparatus.

What is claimed is:

1. An apparatus for surgical treatment of the knee joint, which comprises: two pairs of needles each of which is designed to be driven through one of the joint ends; at least two brace structures in each of which the tips of said needles of one of said pairs are so secured that the brace structure and the needles form a rigid system, one pair of needles with the brace structure secured thereto defining one rigid system to be secured on one joint end, while the second pair of needles and the brace structure secured thereto define a second rigid system to be secured on the other joint end; two distractors rigidly coupled each at one end to one of said rigid systems; and two four-bar linkage means respectively coupling the opposite ends of said distractors to the other rigid system for precisely reproducing the movement of the knee joint while simultaneously maintaining a permanent minimal gap of predetermined magnitude between the joint ends.

2. The combination of claim 1 and wherein each four-bar linkage means includes a portion of each distractor at said opposite end thereof, a pair of links pivotally connected with said portion of said distractor and extending from said portion toward said other brace structure, and a pair of pivot means one of which pivotally connects one of said links to said other brace structure for pivotal movement about an axis coinciding with that one of the needles which is secured to said other brace structure and which is nearest to said one brace structure and the other of which pivotally connects the other link to a portion of said other brace structure which is rigid with said other brace structure.

3. The combination of claim 2 and wherein said portion of each distractor is in the form of a bar extending across each distractor at said opposite end thereof and respectively having free end portions to which said links are pivotally connected.

4. The combination of claim 1 and wherein a bending-unbending means extends between and is removably connected with said brace structures.

* * * * *